United States Patent
Wu (10) Patent No.: US 10,866,399 B2
(45) Date of Patent: Dec. 15, 2020

(54) 3D MEDICAL MICROSCOPE

(71) Applicant: Innostar Service Inc., Taichung (TW)

(72) Inventor: Chih-Meng Wu, Miaoli (TW)

(73) Assignee: Innostar service Inc., Taichung (TW)

(*) Notice: Subject to any disclaimer, the term of this patent is extended or adjusted under 35 U.S.C. 154(b) by 370 days.

(21) Appl. No.: 15/846,121

(22) Filed: Dec. 18, 2017

(65) Prior Publication Data

US 2019/0137748 A1 May 9, 2019

(30) Foreign Application Priority Data

Nov. 8, 2017 (TW) .................................. 106138529

(51) Int. Cl.
| | |
|---|---|
| G02B 21/22 | (2006.01) |
| G02B 21/06 | (2006.01) |
| G02B 21/00 | (2006.01) |
| G02B 21/36 | (2006.01) |
| G02B 27/00 | (2006.01) |

(Continued)

(52) U.S. Cl.
CPC ......... *G02B 21/22* (2013.01); *G02B 21/0012* (2013.01); *G02B 21/06* (2013.01); *G02B 21/361* (2013.01); *G02B 27/0075* (2013.01); *A61B 90/20* (2016.02); *A61B 2017/00212* (2013.01);

(Continued)

(58) Field of Classification Search
CPC .... G02B 21/22; G02B 21/0012; G02B 21/06; G02B 21/361; G02B 21/025; G02B 21/241; G02B 21/18; G02B 21/20; G02B 21/02; G02B 21/04; G02B 21/084; G02B 21/36; G02B 21/362; G02B 27/00; G02B 27/0075; G02B 23/2415; G02B 30/00; G02B 30/10; G02B 30/20; G02B 30/22; A61B 90/20; A61B 90/25; A61B 2090/37; A61B 2090/371; A61B 2017/00212; H04N 13/239; H04N 13/246; H04N 13/254;

(Continued)

(56) References Cited

U.S. PATENT DOCUMENTS

| | | | | |
|---|---|---|---|---|
| 4,674,845 | A * | 6/1987 | Matsumura | ............ G02B 21/22 |
| | | | | 359/377 |
| 2008/0049100 | A1* | 2/2008 | Lipton | ................. H04N 13/144 |
| | | | | 348/43 |

(Continued)

FOREIGN PATENT DOCUMENTS

TW           I580405        *   1/2017

*Primary Examiner* — Stephone B Allen
*Assistant Examiner* — Adam W Booher (57) ABSTRACT

A 3D medical microscope contains: a control unit, a casing, a first lens, a second lens, a reflection unit, and a drive unit. The control unit is configured to control the 3D medical microscope, and the casing includes an accommodation chamber. The first lens is accommodated in the accommodation chamber and is electrically connected with the control unit. The second lens is accommodated in the accommodation chamber and is electrically connected with the control unit, and the first lens and the second lens are located on a horizontal axis. The reflection unit includes a first reflective face and a second reflective face. The drive unit is electrically connected with the control unit and includes a drive motor configured to drive the reflection unit so that the first reflective face and the second reflective face of the reflection unit synchronously move in the vertical direction.

8 Claims, 7 Drawing Sheets

(51) Int. Cl.
  *G02B 21/24* (2006.01)
  *G02B 21/02* (2006.01)
  *A61B 17/00* (2006.01)
  *A61B 90/00* (2016.01)
  *A61B 90/20* (2016.01)

(52) U.S. Cl.
  CPC ...... *A61B 2090/371* (2016.02); *G02B 21/025* (2013.01); *G02B 21/241* (2013.01)

(58) Field of Classification Search
  CPC .. H04N 13/296; H04N 13/243; H04N 13/204; G06T 7/85; G03B 35/00; G03B 35/08
  USPC .......................................... 359/376, 377, 378
  See application file for complete search history.

(56) References Cited

U.S. PATENT DOCUMENTS

| | | | |
|---|---|---|---|
| 2011/0199675 A1* | 8/2011 | Henry | G02B 7/04 |
| | | | 359/376 |
| 2014/0049816 A1* | 2/2014 | Nauli | G02B 21/0012 |
| | | | 359/383 |
| 2017/0351075 A1* | 12/2017 | Ku | G02B 21/0012 |
| 2019/0033568 A1* | 1/2019 | Li | H04N 5/232 |

\* cited by examiner

3D MEDICAL MICROSCOPE

FIELD OF THE INVENTION

The present invention relates to a microscope, and more particularly to a 3D medical microscope which is employed to medicine field so as to adjust viewing distance, to eliminate blind spot, and to shoot images clearly and accurately, when switching magnification and shooting distance.

BACKGROUND OF THE INVENTION

A dual lens stereoscopic microscope is disclosed in TW Patent No. 1580405 and is applicable for surgery. The dual lens stereoscopic microscope contains a casing, an image assembly and an adjustment assembly which are accommodated in the casing. The image assembly includes two lenses and a process chip electrically connected with the two lenses which face downwardly and are rotatably separated. The adjustment assembly has two adjusting units located on two outer sides of the two lenses respectively and are connected with the two lenses. Each of the two adjusting units has a drive motor, a cam, and a limitation element. The drive motor has an actuation shaft, and the cam is eccentrically fitted on the actuation shaft and abuts against the lenses of the drive motor, wherein the limitation element is connected with the casing and one of the lenses so that the lenses abut against the cam. When the cam rotates relative to the actuation shaft, the lenses revolve along a bearing seat relative to the casing, such that angles of the two lenses are adjustable so as to produce depths of field, thus capturing images of three-dimensional (3D) complex tissue (organ) clearly.

A conventional surgical microscope has two lenses configured to capture images and to switch magnification and to adjust shooting distance, but the two lenses shoot images downwardly so switching magnification is limited and blind spot produces. Shooting angle is adjustable by swing the two lenses, yet focusing is not easy to cause poor alignment and sharpness of the images (obscure image). Furthermore, it is inconvenient to calibrate inclination of the two lenses after adjustment by using positioner. Two adjustment units are configured to control the two lenses respectively, thus increasing using space and size of the surgical microscope and shielding operation sight as operating the surgical microscope.

The present invention has arisen to mitigate and/or obviate the afore-described disadvantages.

SUMMARY OF THE INVENTION

The primary aspect of the present invention is to provide a 3D medical microscope in which the first lens and the second lens are fixed horizontally and reflect the lights downwardly via the reflection unit so that the first lens and the second lens are fixed securely when the 3D medical microscope switches the magnification and shooting distance, thus shooting images clearly and accurately and eliminating blind spot.

Secondary aspect of the present invention is to provide a 3D medical microscope in which the first and second lenses are arranged horizontally, thus reducing using space and avoiding shielding operation sight.

Further aspect of the present invention is to provide a 3D medical microscope in which the first lens and the second lens are controlled easily by the drive unit, thus simplifying structure, saving using space, and reducing production cost.

Another aspect of the present invention is to provide a 3D medical microscope which is controlled by the control unit so as to adjust the magnification and to control the 3D medical microscope easily.

To obtain the above aspects, a 3D medical microscope provided by the present invention contains: a control unit, a casing, a first lens, a second lens, a reflection unit, and a drive unit.

The control unit is configured to control the 3D medical microscope.

The casing includes an accommodation chamber.

The first lens is accommodated in the accommodation chamber and electrically connected with the control unit.

The second lens is accommodated in the accommodation chamber and electrically connected with the control unit, and the first lens and the second lens are located on a horizontal axis.

The reflection unit includes a first reflective face and a second reflective face which are housed in the accommodation chamber and are located on a middle of the first lens and the second lens, wherein the first reflective face corresponds to the first lens so that a first optical axis of the first lens turns to reflect lights in a vertical direction, and the second reflective face corresponds to the second lens so that a second optical axis of the second lens turns to reflect the lights in the vertical direction.

The drive unit is electrically connected with the control unit and includes a drive motor configured to drive the reflection unit so that the first reflective face and the second reflective face of the reflection unit synchronously move in the vertical direction.

DETAILED DESCRIPTION OF THE PREFERRED EMBODIMENTS

Figure 1:
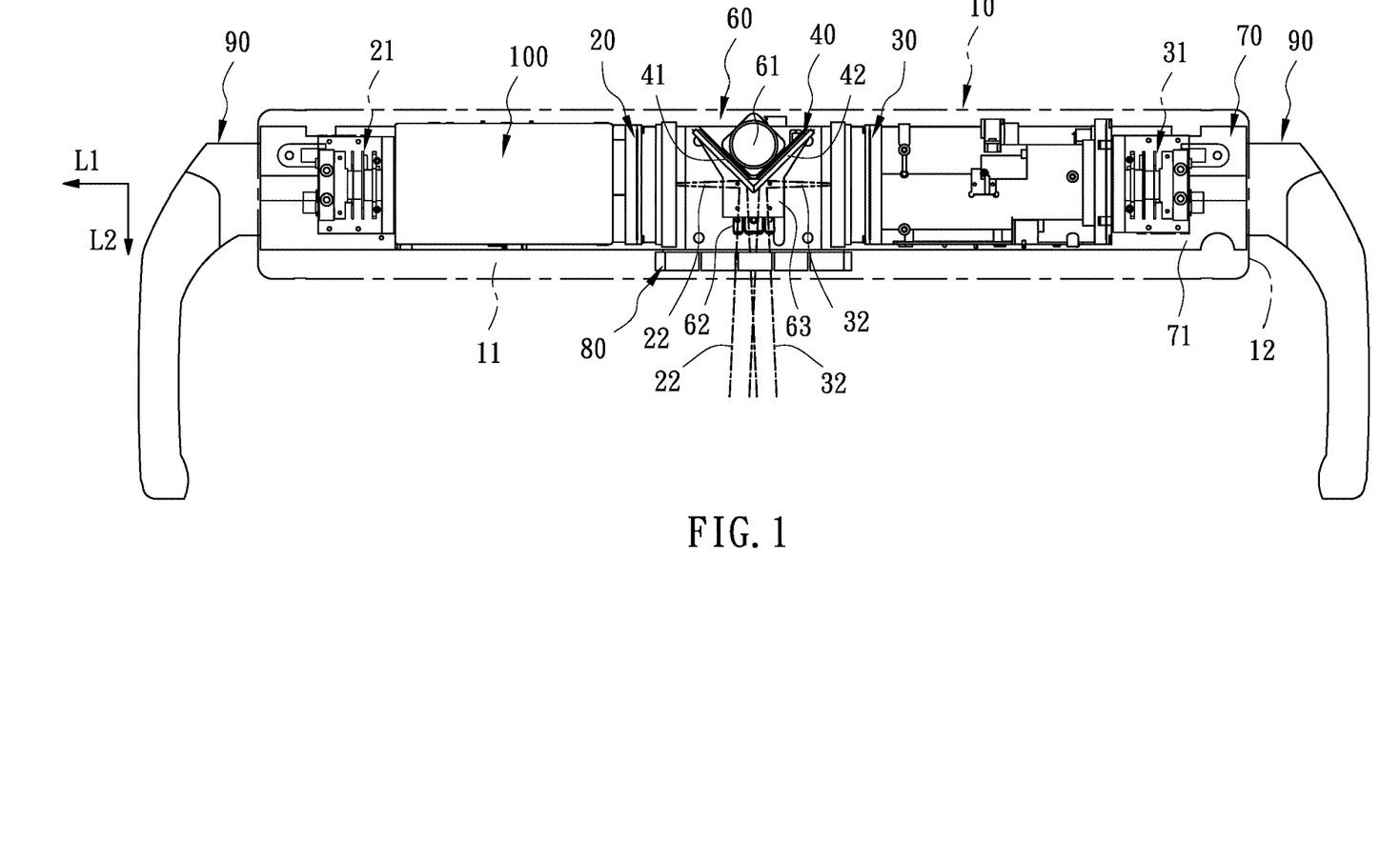
FIG. 1 is a diagram showing the assembly of a 3D medical microscope according to a preferred embodiment of the present invention.

With reference to FIG. 1, a 3D medical microscope according to a preferred embodiment of the present invention comprises: a control unit 100, a casing 10, a first lens 20, a second lens 30, a reflection unit 40, and a drive unit 60.

The control unit 100 is a control circuit configured to control the 3D medical microscope.

The casing 10 includes an accommodation chamber 11.

The first lens 20 and the second lens 30 are accommodated in the accommodation chamber 11 and are electrically connected with the control unit 100. The first lens 20 and the second lens 30 are located on a horizontal axis L1. In this embodiment, the first lens 20 and the second lens 30 are oppositely located on a horizontal axis L1 and are internal zoom lens, wherein the first lens 20 includes a first charge-coupled device (CCD) 21 fixed therein so as to produce a first optical axis 22, and the second lens 30 includes a second charge-coupled device (CCD) 31 mounted therein so as to produce a second optical axis 32.

The reflection unit 40 includes a first reflective face 41 and a second reflective face 42 which are housed in the accommodation chamber 11 and are located on a middle of the first lens 20 and the second lens 30, wherein the first reflective face 41 corresponds to the first lens 20 so that the first optical axis 22 of the first lens turns to reflect lights in a vertical direction L2, and the second reflective face 42 corresponds to the second lens 30 so that the second optical axis 32 of the second lens 30 reflects the lights in the vertical direction L2.

Figure 2:
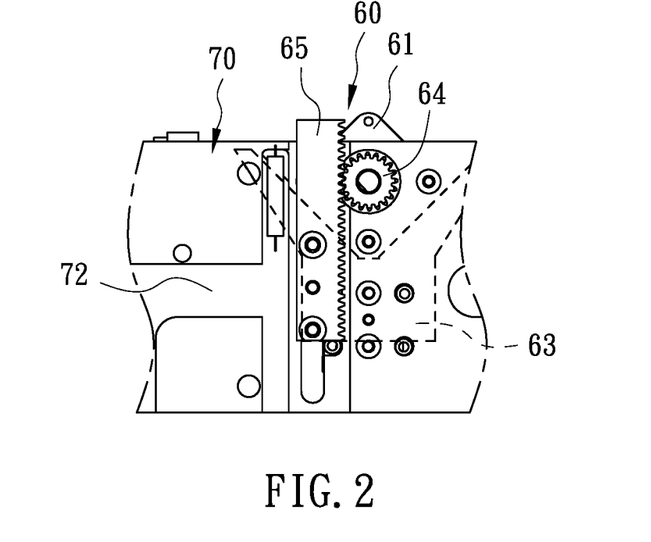
FIG. 2 is a diagram showing the assembly of a part of the 3D medical microscope according to the preferred embodiment of the present invention.

Referring to FIGS. 1 and 2, the drive unit 60 is electrically connected with the control unit 100 and drives the first reflective face 41 and the second reflective face 42 to synchronously move in the vertical direction L2 by way of a drive motor 61. The drive motor 61 is any one of a servo motor, a stepping motor, and an ultrasonic motor. The drive unit 60 includes a slide rail 62, a slider 63, a gear 64, and a rack 65, wherein the gear 64 is coupled with the drive motor 61, and the rack 65 is disposed on the slider 63. The first reflective face 41 and the second reflective face 42 of the reflection unit 40 are two independent lenses respectively and are arranged on the slider 63 in a V shape. When the drive motor 61 is driven to urge the slider 63 to linearly move along the slide rail 62 in the vertical direction L2, the first reflective face 41 and the second reflective face 42 produce depths of field (as shown in FIGS. 4 and 5) individually relative to the first optical axis 22 of the first lens 20 and the second optical axis 32 of the second lens 30.

Figure 6:
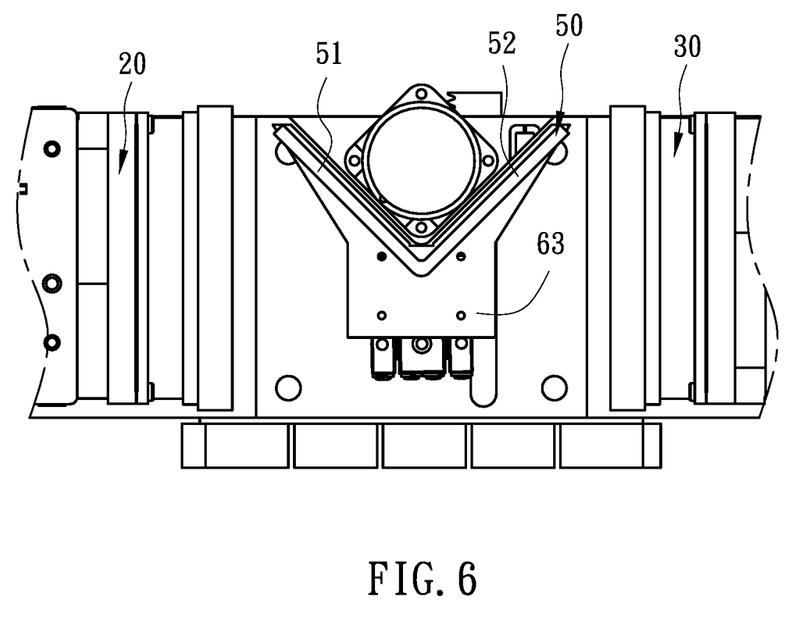
FIG. 6 is another diagram showing the assembly of a part of the 3D medical microscope according to the preferred embodiment of the present invention.

As shown in FIG. 6, the reflection unit 50 is replaced by a V-shaped prism, and the first reflective face 51 and the second reflective face 52 are arranged on the slider 63 in a V shape so that the first reflective face 51 obliquely corresponds to the first lens 20, and the second reflective face 52 obliquely corresponds to the second lens 30 so as to produce depths of field.

Figure 9:
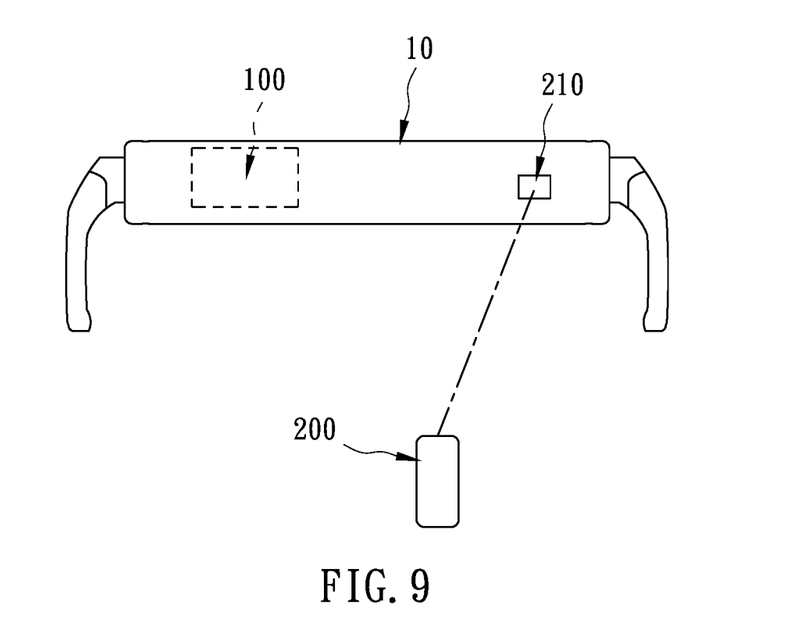
FIG. 9 is a diagram showing the application of the 3D medical microscope according to the preferred embodiment of the present invention.
Figure 10:
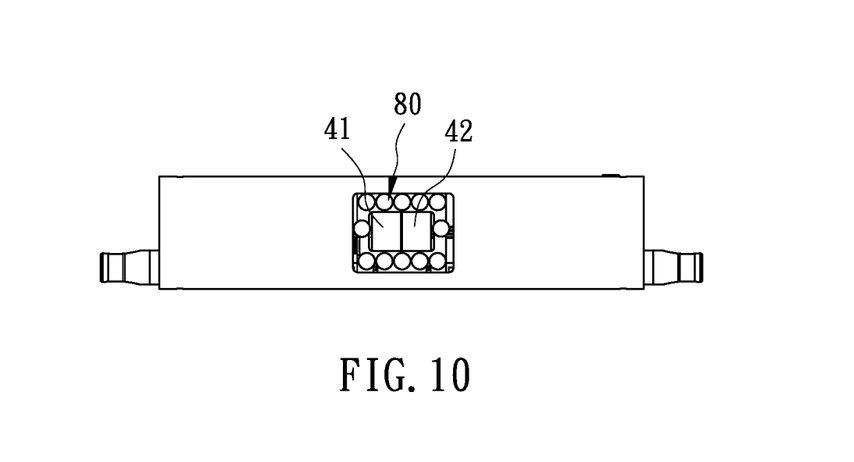
FIG. 10 is another diagram showing the application of the 3D medical microscope according to the preferred embodiment of the present invention.

Referring to FIGS. 1 and 2, the 3D medical microscope further comprises: a fixing plate 70, an illumination assembly 80, and at least one grip 90. The fixing plate 70 is housed in the accommodation chamber 11 of the 10 so as to hold some components. The control unit 100, the first lens 20, the second lens 30, the first reflective face 41 and the second reflective face 42 of the reflection unit 40, the drive motor 61, the slide rail 62, and the slider 63 are held on a first side surface 71 of the fixing plate 70, and the gear 64 and the rack 65 are held on a second side face 72 of the fixing plate 70. As illustrated in FIG. 10, the illumination assembly 80 is mounted below the first reflective face 41 and the second reflective face 42 so that lights are arranged annularly, and the lights from the illumination assembly 80 surrounds the first optical axis 22 and the second optical axis 32 (as shown in FIGS. 4 and 5) so as to supplement the lights. The at least one grip 90 is secured on an external surface 12 of the casing 10. In this embodiment, two grips 90 are fixed on two sides of the external surface 12 of the casing 10 respectively so that user grasps the 3D medical microscope. With reference to FIGS. 1 and 9, the 3D medical microscope further comprises a remote control unit 200 and a receiving unit 210, wherein the receiving unit 210 is mounted on the casing 10 and is electrically connected with the control unit 100, the remote control unit 200 controls the drive unit 60 to operate in a Bluetooth transmission manner, hence the drive unit 60 drives the first reflective face 41 and the second reflective face 42 to move linearly and to control magnification of the first lens 20 and the second lens 30. The remote control unit 200 controls the 3D medical microscope to operate (such as turning on/off the illumination assembly) in a wireless controlling manner.

Figure 3:
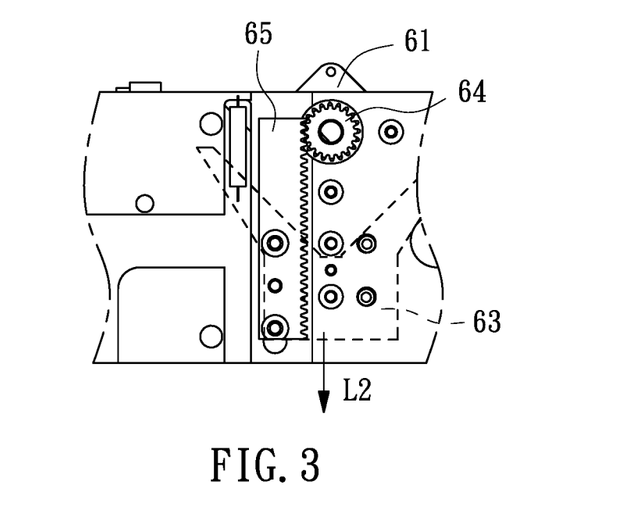
FIG. 3 is a diagram showing the operation of a part of the 3D medical microscope according to the preferred embodiment of the present invention.
Figure 4:
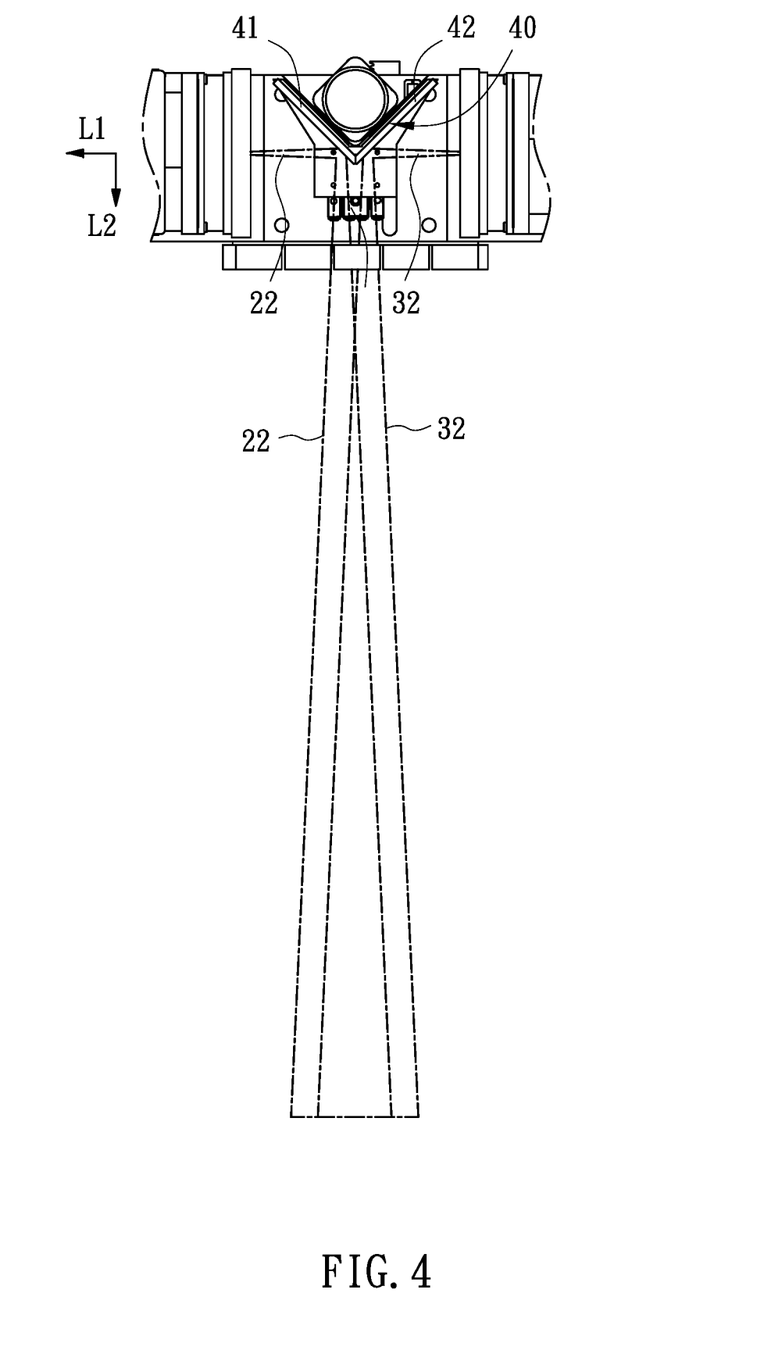
FIG. 4 is another diagram showing the operation of a part of the 3D medical microscope according to the preferred embodiment of the present invention.
Figure 5:
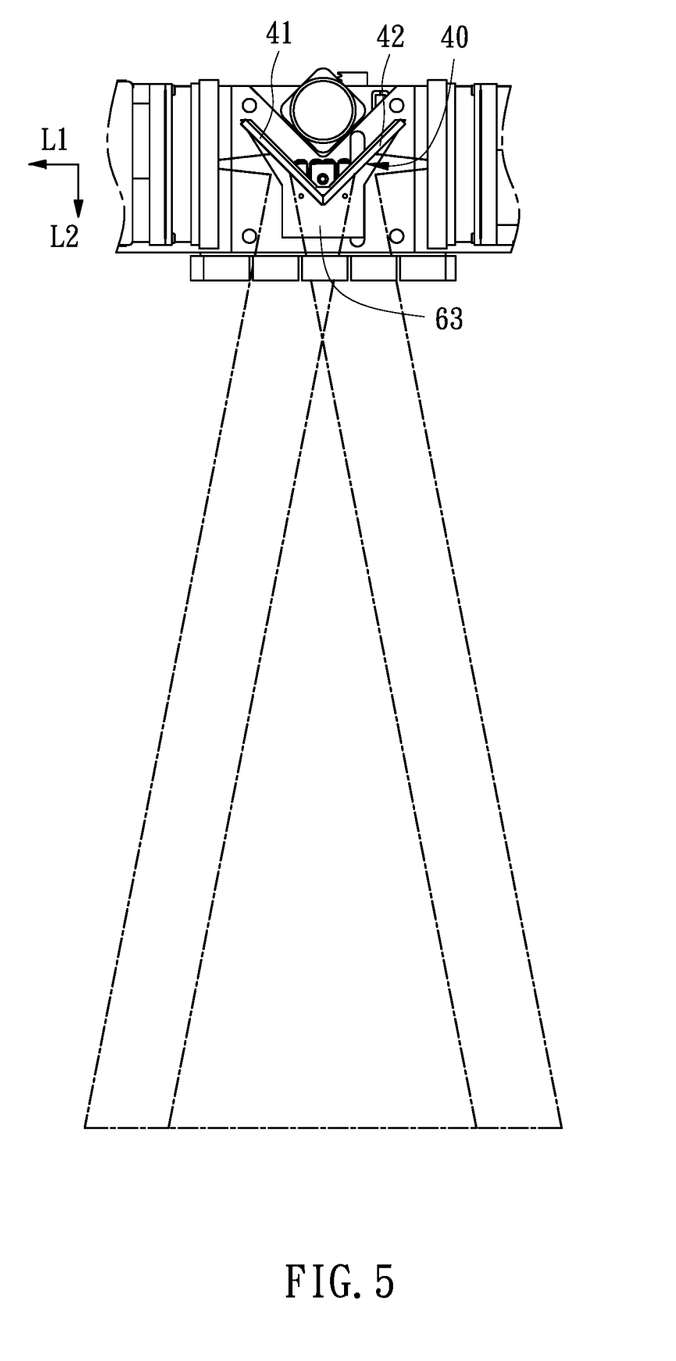
FIG. 5 is also another diagram showing the operation of a part of the 3D medical microscope according to the preferred embodiment of the present invention.

Referring to FIGS. 2 and 4, in operation, when the first reflective face 41 and the second reflective face 42 are located on a starting position, the first optical axis 22 of the first lens 20 and the second optical axis 32 of the second lens 30 illumine the lights onto the first reflective face 41 and the second reflective face 42 along the vertical direction L2, and the first optical axis 22 and the second optical axis 32 reflect to the vertical direction L2 via the first reflective face 41 and the second reflective face 42 individually, in the meantime, the 3D medical microscope operates in a shallow depth of field mode, and the rack 65 is located on an upper original position. Referring to FIGS. 3 and 5, when the drive motor 61 is controlled to rotate, the gear 64 revolves synchronously and drives the rack 65 to move along the vertical direction L2 so as to actuate the slider 62, the first reflective face 41 and the second reflective 42 of the reflection unit 40 move downwardly, and the first optical axis 22 of the first lens 20 and the second optical axis 32 of the second lens 30 are reflected by the first reflective face 41 and the second reflective face 42 widely so as to increase the depths of field. When the first reflective face 41 and the second reflective face 42 move to a lower original position, the 3D medical microscope operates in a deepest depth of field mode.

Figure 7:
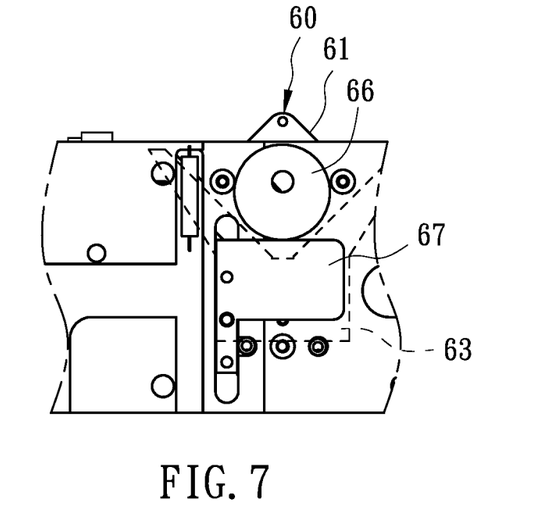
FIG. 7 is a diagram showing the assembly of a part of the 3D medical microscope according to another preferred embodiment of the present invention.
Figure 8:
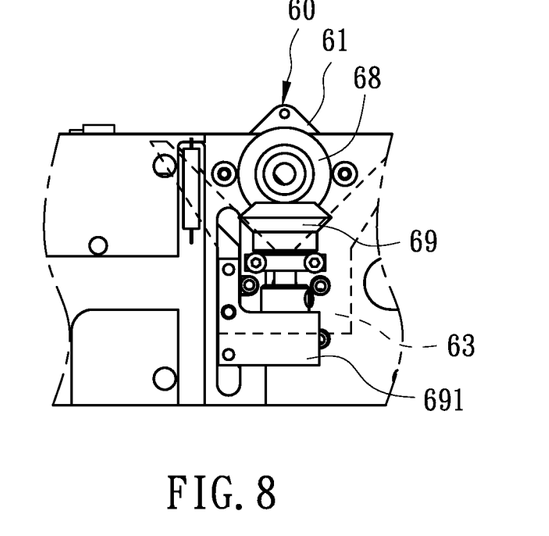
FIG. 8 is a diagram showing the operation of a part of the 3D medical microscope according to another preferred embodiment of the present invention.

As shown in FIGS. 2 and 3, the drive units 60 actuates the reflection unit 40 by using the gear 64 and the rack 65. As illustrated in FIG. 7, the drive unit 60 actuates the reflection unit 40 by way of a cam 66 and a push block 67, wherein the cam 66 is connected with the drive motor 61, the push block 67 contacts with the cam 66 and is mounted on the slider 63 so that the drive motor 61 actuates the cam 66 to rotate and to drive the push block 67, hence the slider 63, the first reflective face 41, and the second reflective face 42 move linearly. Referring to FIG. 8, the drive unit 60 includes a worm gear 68, a worm 69, and a connection seat 691, wherein the worm gear 68 is connected with the drive motor 61, the worm 69 is fixed on the connection seat 691, and the connection seat 691 is secured on the slider 63, such that the drive motor 61 actuates the worm gear 68 to rotate, and the worm gear 68 drives the worm 69 and the connection seat 691 to revolve, hence the first reflective face 41 and the second reflective face 42 move linearly.

Accordingly, the first lens 20 and the second lens 30 are fixed horizontally and reflect the lights downwardly via the first reflective face 41(51) and the second reflective face 42(52) so that the first lens 20 and the second lens 30 are fixed securely when the 3D medical microscope switches the magnification and shooting distance, hence images are clear and accurate. When the 3D medical microscope switches the magnification, it is controlled easily by the control unit 200. Preferably, the drive motor 61 actuates the gear 64 and the rack 65 to drive the slider 63, hence the first reflective face

41(51) and the second reflective face 42(52) move linearly in the vertical direction L2 so as to adjust depths of the field and viewing distance easily. In addition, angels of the first and second optical axes of the first and the second lens are controlled so as to adjust the magnification, thus decreasing related components, a size, and production cost of the 3D medical microscope.

It is to be noted that the first and second lenses are arranged horizontally so that the 3D medical microscope is movably or fixedly supported by a support frame or is mounted on a ceiling in an operating room, thus reducing using space, avoiding shielding operation sight, increasing vertical movement and the depths of field.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A 3D medical microscope comprising:
    a control unit configured to control the 3D medical microscope;
    a casing including an accommodation chamber;
    a first lens accommodated in the accommodation chamber and electrically connected with the control unit;
    a second lens accommodated in the accommodation chamber and electrically connected with the control unit, and the first lens and the second lens being located on a horizontal axis;
    a reflection unit including a first reflective face and a second reflective face which are housed in the accommodation chamber and are located in alignment with a middle of the first lens and the second lens, wherein the first reflective face corresponds to the first lens so that a first optical axis of the first lens turns to reflect lights in a vertical direction, and the second reflective face corresponds to the second lens so that a second optical axis of the second lens turns to reflect the lights in the vertical direction; and
    a drive unit electrically connected with the control unit and including a drive motor configured to drive the reflection unit so that the first reflective face and the second reflective face of the reflection unit synchronously move in the vertical direction;
    wherein the drive unit includes a slide rail and a slider, wherein the first reflective face and the second reflective face of the reflection unit are arranged on the slider, the drive motor drives the slider to linearly move along the slide rail in the vertical direction so that the first reflective face and the second reflective face produce depths of field individually relative to the first optical axis of the first lens and the second optical axis of the second lens.

2. The 3D medical microscope as claimed in claim 1, wherein the drive unit includes a gear and a rack, the gear is coupled with the drive motor, and the rack is disposed on the slider, hence the drive motor actuates the gear to rotate and drives the rack so that the slider, the first reflective face, and the second reflective face move linearly.

3. The 3D medical microscope as claimed in claim 1, wherein the drive unit further includes a cam and a push block, the cam is connected with the drive motor, the push block contacts with the cam and is mounted on the slider so that the drive motor actuates the cam to rotate and to drive the push block, hence the slider, the first reflective face, and the second reflective face move linearly.

4. The 3D medical microscope as claimed in claim 1, wherein the drive unit further includes a worm gear, a worm, and a connection seat, wherein the worm gear is connected with the drive motor, the worm is fixed on the connection seat, and the connection seat is secured on the slider, such that the drive motor actuates the worm gear to rotate, and the worm gear drives the worm and the connection seat to revolve, hence the slider, the first reflective face, and the second reflective face move linearly.

5. The 3D medical microscope as claimed in claim 1, wherein the first reflective face and the second reflective face of the reflection unit are reflecting lenses respectively and are arranged on the slider in a V shape so that the reflective face obliquely corresponds to the first lens, and the second reflective face obliquely corresponds to the second lens.

6. The 3D medical microscope as claimed in claim 1, wherein the reflection unit is a prism, and the first reflective face and the second reflective face are arranged on the slider in a V shape so that the first reflective face obliquely corresponds to the first lens, and the second reflective face obliquely corresponds to the second lens.

7. The 3D medical microscope as claimed in claim 1, wherein the drive motor is any one of a servo motor, a stepping motor, and an ultrasonic motor.

8. The 3D medical microscope as claimed in claim 1 further comprising an illumination assembly mounted below the first reflective face and the second reflective face.

* * * * *